United States Patent [19]

Nebergall et al.

[11] Patent Number: 4,588,399

[45] Date of Patent: * May 13, 1986

[54] CANNULA WITH RADIOPAQUE TIP

[75] Inventors: Perry A. Nebergall, Laguna Hills; Robert C. French, El Toro, both of Calif.

[73] Assignee: Shiley Incorporated, Irvine, Calif.

[*] Notice: The portion of the term of this patent subsequent to Dec. 6, 2000 has been disclaimed.

[21] Appl. No.: 596,069

[22] Filed: Apr. 3, 1984

Related U.S. Application Data

[63] Continuation of Ser. No. 462,907, Feb. 2, 1983, abandoned, which is a continuation of Ser. No. 149,568, May 14, 1980, Pat. No. 4,419,095.

[51] Int. Cl.$^4$ ............................................. A61M 25/00
[52] U.S. Cl. .................................. 604/280; 128/207.15
[58] Field of Search ................. 604/96, 101, 103, 280; 128/207.15; 219/10.41, 10.81

[56] References Cited

U.S. PATENT DOCUMENTS

| | | | |
|---|---|---|---|
| 2,330,399 | 9/1943 | Winder | 128/349 |
| 2,857,915 | 10/1958 | Sheridan | 128/349 |
| 2,930,377 | 3/1960 | Cowley | 128/344 |
| 3,086,525 | 4/1963 | Whitcomb | 128/232 |
| 3,190,290 | 2/1962 | Alley | 128/348 |
| 3,232,810 | 2/1966 | Reesen | 156/273 |
| 3,281,302 | 10/1966 | Kreh et al. | 156/274 |
| 3,360,417 | 12/1967 | Peterson et al. | 156/380 |
| 3,407,817 | 10/1968 | Galleher, Jr. | 128/351 |
| 3,605,750 | 9/1971 | Sheridan et al. | |
| 3,709,227 | 1/1973 | Hayward | 128/351 |
| 3,734,100 | 5/1973 | Walker et al. | 128/351 |
| 3,749,134 | 7/1973 | Slingluff et al. | 138/177 |
| 3,788,328 | 1/1974 | Alley et al. | |
| 3,812,860 | 5/1974 | Gilbert et al. | |
| 3,890,976 | 6/1975 | Bazell et al. | |
| 3,923,580 | 2/1975 | Leatherman | 156/272 |
| 3,941,641 | 3/1976 | Heller, Jr. et al. | 156/272 |
| 3,959,058 | 5/1976 | Rath et al. | 156/272 |
| 3,972,548 | 8/1976 | Roseen | 285/381 |
| 3,989,571 | 11/1976 | Harautuneian | |
| 4,027,659 | 6/1977 | Slingluff | 128/2 |
| 4,276,874 | 7/1981 | Wolver et al. | |
| 4,305,392 | 12/1981 | Chester | 128/207.15 |

FOREIGN PATENT DOCUMENTS

| | | |
|---|---|---|
| 3872070 | 8/1970 | United Kingdom . |
| 1318277 | 5/1973 | United Kingdom . |

Primary Examiner—Stephen C. Pellegrino
Attorney, Agent, or Firm—Knobbe, Martens, Olson & Bear

[57] ABSTRACT

A cannula for insertion into a body cavity, duct, or vessel of a patient includes a parent cannula member and an integral radiopaque tip. The tip is configured so as to be distinguishable from internal body parts in an X ray or flouroscopic image, thus serving to precisely locate the position of the cannula within the patient without substantially obstructing the physician's view of such body parts. The cannula tip and parent member are separately pre-formed from a non-toxic polymeric material and can be constructed so as to have different hardnesses. In one embodiment, the tip is softer than the parent member in order to prevent internal injury to the patient, while in a second embodiment the tip is harder than the parent member for facilitating certain catheterization applications. The pre-formed tip and parent member are then dielectrically heated and welded securely together to form a unitary, integral cannula. The electrodes of the dielectric heating apparatus are connected to dies whose diametrical dimensions conform closely to those of the tip and parent member to provide the present cannula with completely smooth interior and exterior surfaces. In order to prevent the burning of the cannula during this heating process, air is vented from the junction area by providing the outer die with a convex interior surface and by forming longitudinal grooves in the external surface of the inner die or mandrel. The inner mandrel is formed by encapsulating the inner electrode with a highly insulative material to further inhibit burning of the cannula.

9 Claims, 5 Drawing Figures

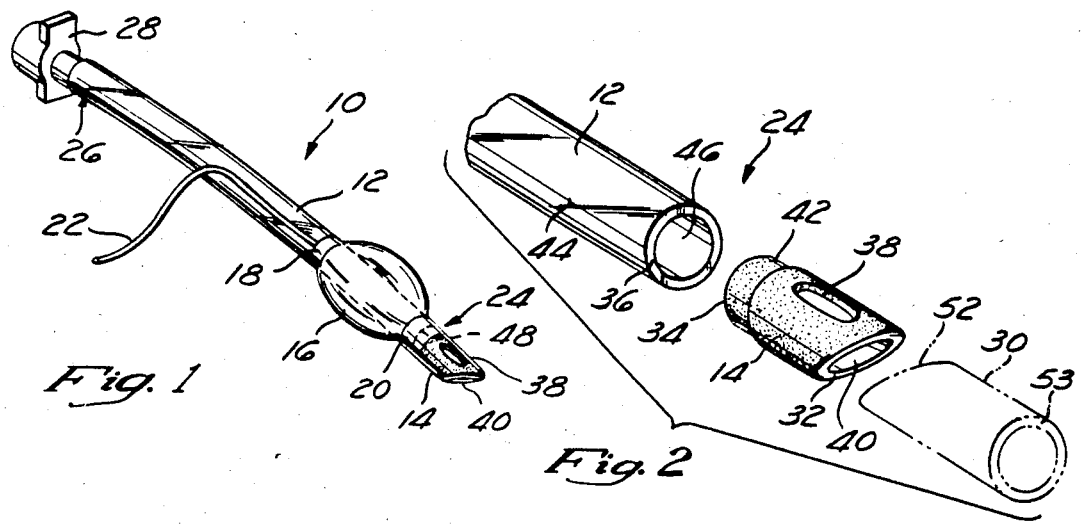
Fig. 1
Fig. 2
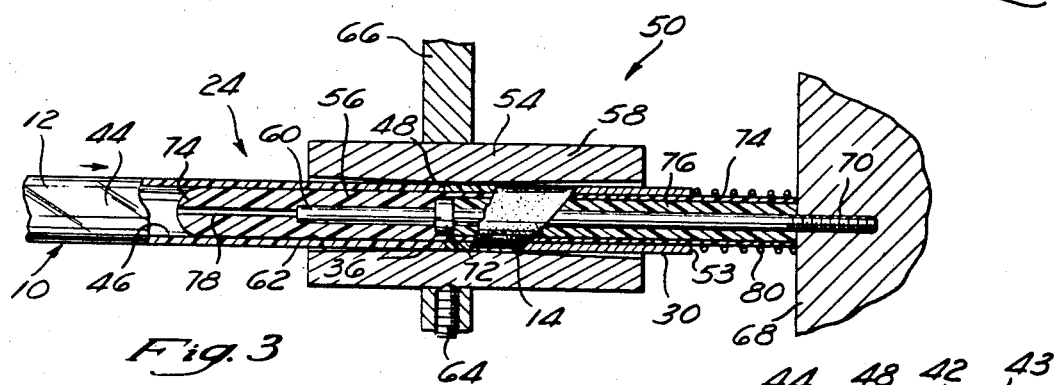
Fig. 3
Fig. 5
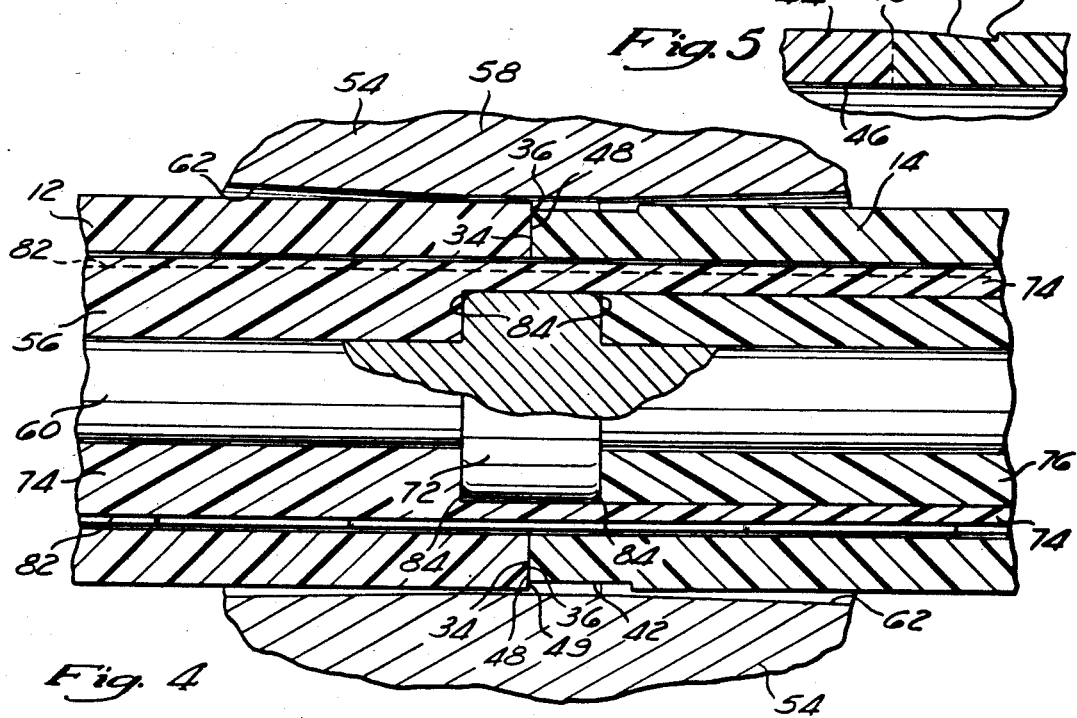
Fig. 4

CANNULA WITH RADIOPAQUE TIP

This application is a continuation of application Ser. No. 462,907, filed Feb. 2, 1983, now abandoned, which is a continuation of application Ser. No. 149,568, filed May 14, 1980, now U.S. Pat. No. 4,419,095.

BACKGROUND OF THE INVENTION

It is common practice in the medical field for a physician to insert a cannula through a natural opening in the patient's body, such as the nasal or oral openings, or through an incised opening, and to advance the cannula to a particular location within the body. For example, such a cannula may take the form of an endotracheal tube. The distal end of the tube is typically inserted through the oral or nasal openings of the patient, advanced past the larynx and pharynx and positioned in the trachea. The proximal end of the endotracheal tube remains outside of the patient's body and can be attached to respiratory equipment, in order to assist the patient's breathing, or to anesthetic equipment so that anesthetic gas can be administered to the patient prior to surgery.

Another example of cannulas placed within the body is a tracheostomy tube, such as the outer diameter described and claimed in the U.S. Pat. No. 3,693,624, assigned to Shiley, Inc., assignee of the present invention. Such tracheostomy tubes are generally inserted into the trachea of the patient through an incision in the neck. Other cannulas in common used today include catheters, which are inserted into ducts or vessels within the patient's body. Specifically, a cardiac catheter may be inserted into a blood vessel and abrasively passed along the interior walls of the vessel in order to remove fatty cholesterol accumulation thereon.

In order to properly place these cannulas, and especially their distal tips, within the body so that they will accomplish their intended purpose without injuring the patient's internal tissue, a physician or radiologist typically utilizes an X ray photograph or a fluoroscope to examine the location of the cannula within the body. In fact, it is common in the internal placement of some cannulas, e.g. endotracheal tubes, to utilize a fluoroscope to visually monitor the location of the cannula as it is inserted and placed within the body. Therefore, it is necessary that the cannula (or some portion of it) be radiopaque.

Certain prior cannulas, however, were constructed so as to be entirely radiopaque. Thus, placement of the cannula by the physician or radiologist was hindered since the radiopaqueness of the cannula obscured visual inspection of the cannula's position with respect to surrounding organs and tissue. Furthermore, such completely radiopaque cannulas precluded the use of a clear material in constructing the cannula, thereby disadvantageously preventing the use of a common diagnostic technique involving the visual examination of fluids or other matter that may accumulate within the proximal, external portion of the cannula.

Other cannulas presently in use are completely clear, except for their distal ends which are provided with a radiopaque marker to indicate the location of the cannula without obscuring the view of surrounding body parts. To provide such markers, thin strips or rings made of radiopaque materials, such as metal, are embedded in the cannula near its tip. Such radiopaque inserts, however, resemble many similarly shaped body parts, and are therefore difficult to distinguish from such parts in an X ray or fluoroscopic image. Thus, the location of the cannula within the body is very difficult to determine, posing a risk of injury to the patient.

Even if the inserts are identified apart from surrounding body parts, the orientation of such small geographic shapes can be confusing, preventing the physician or radiologist from precisely locating the cannula tip. Furthermore, it is possible for such inserts, not being integral parts of the cannula, to become separated from the cannula and cause injury to the patient. Still other cannulas in common use have a radiopaque tip bonded to the distal end of the cannula by means of a solvent or adhesive. Again, however, since the cannula is not a unitary device, detachment of the tip within the patient's body poses a serious threat to the health and safety of the patient.

SUMMARY OF THE INVENTION

The present invention relates to a composite cannula having a radiopaque tip integrally formed on its distal end. The distinct configuration of the tip is such that it cannot be mistaken for internal bodily parts and does not substantially obstruct the physician's view of the location of the cannula within the body. Thus, the present invention provides precise location and orientation of the cannula tip relative to the patient's internal anatomy, facilitating insertion and placement of the cannula within the body and preventing injury to the patient. Furthermore, a number of different types of cannulas, including endotracheal tubes, tracheostomy tubes, catheters, and the like, can be constructed in accordance with the principles of the present invention.

To further prevent injury, one embodiment of the cannula of the present invention includes a tip which is softer than the parent member to which the tip is integrally attached. In a second embodiment, the tip is harder than the parent member in order to enhance the efficiency of the cannula in particular applications, such as the catheterization of a blood vessel to remove cholesterol accumulations. Although the hardness of the tip may advantageously vary, depending upon the application or purpose of the cannula, the hardness of the parent member can be such that it remains sufficiently rigid, in order to facilitate insertion and placement of the cannula.

A significant feature of the present invention is that the radiopaque tip and parent member are separately pre-formed and then dielectrically welded or fused together to form a unitary, composite cannula. In fact, the tensile strength of the joint between the tip and parent member is substantially the same as that of the parent member. Thus, the fear or danger of detachment of the tip within the patient's body is eliminated. Furthermore, the independent construction of the tip and parent member permits the latter to be made from a clear material, thus permitting visual inspection of any matter collected in that portion of the cannula which remains outside of the patient's body.

The tip and parent member of the present invention are joined in such a manner as to provide a cannula whose interior and exterior surfaces are completely smooth. That is, the inner and outer diameters of these mated elements are uniform and therefore do not produce any projecting edges or ridges at the joint. The smooth interior surface of the present cannula advantageously inhibits the accumulation of mucus or other bodily secretions within the bore of the cannula. Moreover, the smooth exterior surface of the cannula eliminates irritation and injury to delicate internal tissue. In this regard, the external surface of the tip is also provided with a reduced diameter so that the attachment of an inflatable cuff, such as that commonly utilized in endotracheal tubes and tracheostomy tubes, near the distal end of the cannula will not ruin the smoothness of its exterior surface.

Any one of a wide variety of non-toxic, polymeric materials can be used in the construction of the tip and parent member. In selecting a particular material, several factors may be considered, such as the specific application of the cannula, the economics of its manufacture, and its feasability as a disposable item. Prior to the construction of the tip, the tip material is blended with a suitable non toxic, radiopaque material. The tip can then be pre-formed by means of any one of a number of suitable techniques, such as injection or compression molding or extrusion and end-forming. Alternatively, casting or slush molding processes can be utilized.

The tip and parent member of the cannula of the present invention are integrally fused or welded together by means of a specially designed dielectric heating apparatus. This apparatus is capable of passing a pulsating direct electrical current having an extremely high frequency, e.g. within the range normally referred to as the radio frequency and between a pair of inner and outer electrodes so that the current passes through the mated ends of the tip and parent member. The ends are thus heated to a temperature sufficient to cause them to liquify or melt, and, upon cooling, they are fused together to form a unitary cannula.

The outer electrode of this dielectric heating apparatus also serves as an annular die to shape and form the molten material of the cannula during fusion. This outer die closely surrounds the distal end of the cannula, including the tip and the junction area between the tip and the parent member. The cylindrical interior surface of this outer die is slightly convex, and the die is positioned over the cannula so that its smallest inner diameter is located at the joint. Thus, the clearance between the die and the mating elements is very small at the joint but gradually increases toward each end of the die. This construction advantageously concentrates the dielectrically produced heat at the critical joint and junction areas, while at the same time permitting the hot, expanding air in the junction area to escape.

The inner electrode is encapsulated in a highly insulative material to form an inner die or mandrel which is positioned within the cannula so that it is generally opposite the outer die. A large collar is formed on the inner electrode so as to be adjacent the joint, thus serving to concentrate the heat produced by the dielectric device at this location. Furthermore, the exterior surface of this mandrel or inner die is longitudinally grooved in order to vent the hot surrounding air during the fusion process. The outer diameter of the mandrel is just slightly less than the inner diameter of the cannula so that, like the outer die, the intersticial space between the mandrel and the interior surface of the cannula is very small.

This radio frequency, dielectric welding apparatus enjoys several significant advantages. For example, the carefully configured dies, whose dimensions conform very closely to those of the tip and parent member, form the heated, softened material of these mated elements during the welding process in order to provide the completely smooth interior and exterior surfaces of the cannula of the present invention. Furthermore, due to the configuration of the dies and the electrodes, which extend across the entire junction area while concentrating the heat at the joint, the present dielectric apparatus advantageously eliminates dimensional differences and other irregularities between the tip and parent member. Such differences include any projecting edges or ridges which may be created at the joint due to differences in the respective inner or outer diameters of the mated elements. Moreover, irregularities in the mating surfaces of the tip and parent member are eliminated in part by exerting an axial force on the tip to press it against the distal end of the parent member. This force can be provided by a spring bearing against a back up plug positioned next to the tip, or by any other suitable means. Thus, the mating surfaces of the tip and parent member need not be true, greatly facilitating both their manufacture and assembly and reducing the expense associated with these operations.

Another important advantage of the present dielectric apparatus is that, in spite of only slight clearances between the dies and the surfaces of the cannula, it integrally joins the tip to the parent member without burning or scorching either element. Since air and water are better electrical conductors than the materials from which the present cannula can be constructed, burning is prevented by insuring that the tip and parent member are completely dry and by providing means on both dies for venting the air from the interstices between the dies and these mated elements. Burning is further precluded by encapsulating one of the electrodes, preferably the inner electrode, in a highly insulative material. Moreover, the edges of the collar on the inner electrode are rounded in order to prevent the arching of the current generated by the present dielectric apparatus, further inhibiting the burning of the cannula material.

DESCRIPTION OF THE DRAWINGS

FIG. 1 is a perspective view of the cannula of the present invention, in this case an endotracheal tube, having a radiopaque tip;

FIG. 2 is an exploded view of the distal end of the present cannula, including a parent member and a radiopaque tip, and a back up plug used in dielectrically joining these elements;

FIG. 3 is a side cross sectional view of the present cannula and the dielectric heating apparatus utilized in fusing the parent member and radiopaque tip together;

FIG. 4 is a close up view of the junction area and the parent member and radiopaque tip before they are fused together; and FIG. 5 is a close up view of the joint after fusion of the parent member and tip.

DETAILED DESCRIPTION OF THE INVENTION

Referring initially to FIG. 1, there is shown the composite cannula 10 of the present invention including a parent member 12, in this case an endotracheal tube, and an integral radiopaque tip 14. Although the principles of the present invention are illustrated in connection with an endotracheal tube, it is to be understood that they can also be applied to a wide variety of cannulas, such as tracheostomy tubes, catheters, and the like. Specifically, the cannula 10 of the present invention may take the form of a tracheostomy tube having a disposable inner cannula, such as that described and claimed in U.S. Pat. No. 4,419,095, issued Dec. 6, 1983 and assigned to Shiley, Inc., assignee of the present invention.

Attached to the parent member 12 of the present cannula 10, at a location just behind the radiopaque tip 14, is an inflatable cuff 16. When inflated, this cuff 16 provides an air tight seal between the endotracheal tube 10 and the inner walls of the trachea. Each end of the cuff 16 is attached to the parent member 12 so as to form front and rear sleeves 18 and 20, respectively. The cuff 16 is inflated by means of a flexible inflation tube 22 which extends through a small lumen in the wall of the endotracheal tube 10 and into the cuff 16. Shown attached to the proximal end 26 of the parent member 12 is an endotracheal tube connector 28 which is described and claimed in U.S. Pat. No. 4,146,034, assigned to Shiley, Inc. This connector 28 is used to connect the endotracheal tube 10 to respiratory or anesthetic equipment (not shown).

FIG. 2 is an exploded view of the distal end 24 of the present unitary cannula 10, including its constituent elements, the parent member 12 and a radiopaque tip 14. Shown in dotted lines is a back up plug 30 which is utilized in fusing these two elements together, as will be explained in more detail below. The radiopaque tip 14 is provided with a beveled, distal end 32 and a flat, non-beveled proximal end 34, which mates with the distal end 36 of the parent member 10. An oblong-shaped fenestration 38 is formed in the side of the tip in order to provide an alternate exit for gas or liquid in the event that the main opening 40 of the cannula 10 should become clogged with mucus or lodged against an internal bodily wall or organ.

As shown in FIG. 2, the proximal end 34 of the tip 14 is also characterized by an annular section 42 having a reduced diameter. The location of this section 42 is such that it accommodates the front sleeve 20 of the cuff 16 so that the attachment of the sleeve 20 does not create a raised ridge around the exterior surface 44 of the cannula 10. This construction maintains the smoothness of the cannula's exterior surface 44 and prevents any irritation or abrasion to internal tissues that could be caused by such a ridge during insertion and placement of the cannula 10 within the patient.

The configuration of the radiopaque tip 14 of the cannula 10 of the present invention is such that it can be easily distinguished, in X rays or fluoroscopic images, from internal bodily parts. Furthermore, since the entire tip 14 of the present cannula 10 is radiopaque, rather than a mere line on the side of the tip or a ring encircling the opening 40, the precise orientation of the tip 14 with respect to such internal bodily parts can be easily determined. Therefore, the radiopaque tip 14 of the present invention greatly facilitates insertion and placement of the present cannula 10 and prevents internal injury or discomfort to the patient.

The parent member 12 and tip 14 of the present cannula 10 are separately pre-formed from compatible materials which are capable of being welded or fused together. A number of flexible, biologically safe, polymeric or elastomeric materials can be utilized in the construction of the present cannula, with the specific selection of the material depending primarily upon the application of the cannula and the desired cost of its manufacture. Such suitable materials include, but are not limited to polyvinyl chloride, polyurethane, silicone rubber, latex, polyamides, etc. In order to produce the radiopaqueness of the tip 14, the tip material is blended with a suitable non-toxic radiopaque substance, preferably bismuth trioxide or a barium compound. The tip 14 can also be constructed by any one of a number of suitable methods. For example, it may be injection or compression molded or extruded and then dielectrically end formed. Alternatively, casting or slushing processes may be utilized. The parent member 12 is typically extruded from a clear material (in order to permit visual examination of its contents) although other manufacturing techniques can also be employed.

An important advantage of separately pre-forming the parent member 12 and tip 14 of the present cannula 10 is that these elements can then be constructed to have different hardnesses. For example, in certain cannulas such as endotracheal tubes and tracheostomy tubes, the tip 14 can be made softer than the parent member 12 in order to prevent pain and injury to the patient. At the same time, the parent member 12 can remain sufficiently rigid to facilitate insertion of the cannula 10. The difference in hardnesses, however, between the parent member 12 and the tip 14 is sufficiently small to permit the use of a dielectric process, explained in more detail below, to fuse them together. Thus, it has been found that a cannula 10 in which the parent member 12 has a Shore A hardness factor of about 85 to 95, and the tip 14 has a Shore A factor of about 10 less than its respective parent member 12, provides an optimum in both tip softness and parent rigidity. Furthermore, when desirable, the present cannula 10 can be constructed so that the tip 14 is harder than the parent device 12.

Referring again to FIG. 2, despite being constructed by joining two distinct elements having different hardnesses, the cannula 10 of the present invention is provided with completely smooth surfaces. Thus, the smoothness of the interior and exterior surfaces 46 and 44, respectively, of the parent member 12 continues across the joint 48 between the tip 14 and parent member 12 (shown in a dotted line in FIG. 1 beneath the front sleeve 20) to provide a continuous, uniformly dimensioned cannula 10. As explained above, the smooth interior surface 46 inhibits the accumulation of mucus within the cannula 10 and the smoothness of the exterior surface 44 prevents irritation and injury to delicate internal tissue.

FIGS. 3 and 4 cross-sectionally illustrate a dielectric heating apparatus 50 for integrally welding the radiopaque tip 14 to the parent member 12. With reference initially to FIG. 3, this dielectric apparatus 50 is shown engaging the distal end 24 of the present cannula 10, including the parent member 12, the tip 14, which is mated with the parent member 12 at the joint 48, and the back up plug 30 (shown in FIG. 2). The joint 48 and junction area between the parent member 12 and tip 14 are shown in more detail in FIG. 4. The back up plug 30 is provided with a beveled proximal end 52, as shown in FIG. 2, which corresponds with the beveled distal end 32 of the tip 14, and a flat distal end 53. The proximal end 52 of the plug 30 is positioned against the tip 14 to maintain its proper orientation relative to the parent member 12 during the fusion process.

The dielectric heating apparatus 50 includes an outer annular die 54, which also serves as an outer electrode 58, and an inner cylindrical die or mandrel 56, which encapsulates a long, rod-like electrode 60.

As shown in FIG. 3, the outer die 54 is positioned over and closely surrounds the junction area of the cannula 10, including the distal end 36 of the parent member 12, the tip 14, and a portion of the back up plug 30. The interior surface 62 of this outer die 54 is slightly convex, as shown more clearly in FIG. 4, so that its smallest inner diameter is adjacent the joint 48 while its largest inner diameter is located at its opposite ends. A set screw 64 connects this outer die 54 to a collar 66 which in turn is connected to a terminal of the generator of the dielectric apparatus 50. Preferably, the outer die 54 is constructed from a conductive metal, such as brass or beryllium copper, to permit it to serve simultaneously as an electrode 58.

Referring again to FIG. 3, the inner die or mandrel 56 is shown inserted through the back up plug 30, the radiopaque tip 14, and into the distal end 36 of the parent member 12. The encapsulated inner electrode 60 is positioned generally opposite the outer electrode 58 and extends almost the entire length of the mandrel 56. This inner electrode 60 makes contact with a metal plate 68 which in turn is connected to a terminal of the generator of the dielectric heating apparatus 50. Preferably, the inner electrode 60 is connected to the negative terminal of the generator and the outer electrode is connected to the positive terminal of the generator, although this configuration can be reversed. Contact between the inner electrode 60 and the metal plate 68 can be made by any suitable means, such as the threaded engagement 70 shown in FIG. 3. The inner electrode 60 is also provided with an annular collar 72 which is located directly adjacent the joint 48.

As seen more clearly in FIG. 4, the mandrel 56 is comprised of two parts: a hollow outer shell 74, which houses the electrode 60, and an inner tubular member 76, which fits tightly over the electrode 60 and within the shell 74. To assemble the mandrel 56, the electrode 60 is first inserted into the shell 74 and then held securely in place by fitting the tubular member 76 over the electrode 60 so that it also fits within the shell 74. These parts fit tightly around the electrode 60 in order to prevent the presence of air within the mandrel 56. Therefore, in order to facilitate the assembly of the mandrel 56, the shell 74 is provided with a vent channel 78 in its distal end (shown in FIG. 3) and the outer surface of the electrode 60 is grooved (not shown), thus permitting the displacement of the air as the electrode 60 and tubular member 76 are inserted into the shell 74.

The mandrel 56 is constructed from a material having a high dielectric constant, preferably Teflon (a trademark of the Dupont Company), although other insulative materials such as lexan or polypropylene styrene are also suitable. These insulative materials are advantageously unaffected by the high frequency current generated by the dielectric heating apparatus. Similarly, the back up plug 30 is preferably constructed from a poor conductor of radio frequency electric current, such as one of the materials just mentioned.

FIG. 3 illustrates in cross-section a spring 80, one end of which bears against the metal plate 68 of the dielectric heating apparatus 50 while its other end bears against the flat distal end 53 of the back up plug 30. This spring 80 applies, through the back up plug 30, a force of 20-35 pounds per square inch to the radiopaque tip 14 in order to hold the tip 14 securely in place during its fusion to the parent member 12. The spring 80 also serves to pressurize the joint 48 to eliminate the air within it and to facilitate the elimination of dimensional differences between the mating surfaces 34 and 36 of the tip 14 and parent member 12, as will be described in more detail below. Other equivalent pressurizing means, such as an air cylinder, can also be utilized. This spring 80 is preferably constructed from a non-inductive metal, such as beryllium copper, so as to be unaffected by the current generated by the dielectric heating apparatus 50.

As also shown in FIG. 3, the outer die 54 and mandrel 56 of the dielectric apparatus 50 conform very closely to the diametrical dimensions of the parent member 12. That is, the inner diameter of the outer die 54 closely approximates the outer diameter of the parent member 12, and the outer diameter of the mandrel 56 is substantially the same as its inner diameter. Thus, during the fusion of the tip 14 to the parent member 12, these elements are molded and formed by these dies 54 and 56 so as to be dimensionally uniform with the parent member 12. In fact, the heated surfaces 44 and 46 of the cannula 10 tend to swell at the joint 48 and, if not constrained by the dies 54 and 56, would form a raised ridge or mound at this point. Thus, the configuration of the dies 54 and 56 of the dielectric heating apparatus 56 produces a cannula 10 having smooth, uniformly dimensioned surfaces 44 and 46.

Furthermore, as illustrated in FIGS. 3 and 4, the smallest inner diameter of the outer electrode 58 is located at the joint 48 and the largest outer diameter of the inner electrode 60, which is provided by the collar 72, is directly adjacent the joint 48. This construction permits the heat generated by the dielectric apparatus 50 to be concentrated at the joint 48. Thus, as the cannula material melts in response to this heat, dimensional differences between the tip 14 and the parent member 12 and irregularities in the smoothness of their mating surfaces 34 and 36 are eliminated. For example, the inner and outer diameters of these mating elements need not be identical nor do the mating surfaces 34 and 36 have to be precisely parallel or flush. Moreover, the elongate configuration of the inner and outer electrodes 60 and 58, respectively, insures that heat will be generated completely across the junction area, and not at the joint 48 only, further eliminating dimensional irregularities between the tip 14 and parent member 12.

FIGS. 4 and 5 illustrate the manner in which the present dielectric heating apparatus 50 eliminates differences in the inner and outer diameters of the parent member 12 and radiopaque tip 14. FIG. 4 illustrates the joint 48 prior to the fusion of these two elements together. Thus, the area of reduced diameter 42 on the tip 14 forms an annular ridge 49 at the joint 48 because it causes the outer diameter of the mating surface 34 of the tip 14 to be less than the outer diameter of the mating surface 36 on the parent member 12. During fusion of the tip 14 to the parent member 12, however, this area of reduced diameter 42 expands or swells at the joint 48 (due to the concentration of heat at this location) so that the outer diameters of the mating surfaces 34 and 36 are equal. Thus, following fusion of the tip 14 to the parent member 12, as illustrated in FIG. 5, the ridge 49 at the joint 48 is eliminated to provide a smooth exterior surface 44 on the cannula 10. Furthermore, a portion of the area of reduced diameter 42 advantageously remains after fusion, as indicated at 43 in FIG. 5, since it is not within the area of heat concentration created between the outer electrode 58 and the inner collar 72. Therefore, this reduced area 43 receives the front sleeve 20 of the cuff 16 so that the smoothness of the exterior surface 44 of the cannula 10 is maintained.

Thus, the dielectric heating apparatus 50 produces a cannula 10 having completely smooth interior and exterior surfaces, 46 and 44, respectively. There are no projecting edges or ridges at the joint 48, or anywhere else, that could act as focal points for the accumulation of mucus or other bodily secretions. Furthermore, since the mating surfaces of the tip 14 and parent member 12 need not be exactly flush or true, the manufacture and assembly of these elements are greatly facilitated.

These results are aided by the action of the spring 80 shown in FIG. 3. Besides holding the tip 14 securely in place during its fusion to the parent member 12, the spring 80 exerts a force at the joint 48 which facilitates the elimination of differences in the mating surfaces of these elements by forcing them together while they are in a melted, softened state. Furthermore, the axial force provided by the spring 80 insures a strong, secure union between the tip 14 and parent member 12.

FIG. 4 illustrates the features of the dielectric heating apparatus 50 which prevents the burning or scorching of the tip 14 and parent member 12 as they are welded together to form the present cannula 10. Since air and water are better conductors of the electric current generated by the dielectric apparatus 50 than the cannula material, it is important that these elements be eliminated from the joint 48 and junction area. Thus, prior to the fusion of the tip 14 to the parent member 12, both parts are thoroughly dried.

Furthermore, during fusion, the hot expanding air existing in the junction area is vented from the interstices between the dies 54 and 56 and the cannula 10 in order to prevent burning. Such venting is accomplished outside of the cannula 10 by the tapered, convex interior surface 62 of the outer die 54 which permits air to escape the junction area by means of its gradually increasing inner diameter. Inside the cannula 10, air is vented by means of longitudinal grooves 82, shown in FIG. 4, formed in the exterior surface of the mandrel 56. Moreover, as described above, the mandrel 56 is assembled so as to substantially eliminate any air existing within, and it is air tight in order to prevent the entrance of air. Lastly, any air existing in the joint 48 will be forced out by the pressure exerted by the spring 80. Once eliminated from the joint 48, this air will be vented from the junction area along the channels described above.

Burning is also prevented, in spite of the close proximity between the electrodes 58 and 60 of the cannula 10, by encapsulating one electrode in a highly insulative material. In the preferred embodiment, the inner electrode 60 is encapsulated in such an insulative material so as to form the mandrel 56 shown in FIGS. 3 and 4. This construction advantageously permits the cannula 10 of the present invention to conform to the shape of the mandrel 56, thereby providing a smooth interior surface 46, while at the same time insulating that surface to prevent it from burning.

As clearly shown in FIG. 4, the edges 84 of the collar 72 on the inner electrode 60 are rounded. Sharp corners and edges provide jumping off points for the radio frequency electric current to arch across to the outer elcctrode 58. By rounding the edges 84 of the collar 72, such arcing is prevented and the burning of the surfaces of the cannula 10 is further inhibited.

In operation, the dielectric heating apparatus 50 generates a high frequency electric current which passes between the electrodes 58 and 60 and through the mated ends of the tip 14 and parent member 12. The heat generated by the dielectric apparatus 50 is concentrated at the joint 48, but also exists across the junction area due to the extended configuration of the electrodes 58 and 60. This heat causes the tip 14 and parent member 12 to partially liquify or melt, and as they cool and harden, they are welded to one another. During this fusion process, however, the joint 48 becomes homogenous, both structurally and dimensionally, as explained above. Thus, the radiopaque tip 14 is integrally attached to a non-radiopaque parent member 12 to form a unitary cannula 10 whose tensile strength at the joint 48 and junction area is substantially the same as the remainder of the cannula 10. This strength permits the cannula 10 to be advantageously thin-walled; that is, having a maximum inner diameter and a minimum outer diameter.

The radio frequency current produced by the dielectric heating apparatus 50 is a conventional pulsating DC current and is passed through the cannula 10 for only a very short time, e.g. about one-half second, although this time will vary depending upon the size and wall thickness of the cannula 10. However, this heating time must be carefully controlled so that the cannula 10, and particularly the tip 14 which is generally softer than the rest of the cannula 10, does not liquify too much and begin to flow.

The power necessary to generate this heating current can be determined by the following equation:

$$P = 1.41[E/d]^2 fe' \tan \delta$$

Where P is power (in watts/in$^3$), E is the voltage across the electrodes (in kilovolts), f is the frequency (in mega-Hertz), e' is the dielectric constant of the cannula material, tan $\delta$ is the dissipation factor of the cannula material, and d is the distance (in inches) between the outer electrode 58 and the collar 72 on the inner electrode 60. As merely one example, the required power may fall within a range of 400-600 watts with the frequency being 40-95 megaHertz, although these figures may vary widely depending on the thickness and material of the cannula wall and the overall diameter of the cannula.

Thus, in conclusion, the dielectric heating apparatus and method for using it provides the unitary cannula of the present invention with an integral radiopaque tip. Although this apparatus and the cannula itself have been illustrated in connection with a cylindrical cannula, cannulas of other configurations and shapes can also be formed in accordance with the principles of the present invention. Furthermore, the cannula of the present invention can also be constructed by using other suitable heating and joining techniques, such as induction or impulse heating and ultrasonics.

What is claimed is:

1. A composite cannula adapted for use with an inflatable cuff, said cuff having distal and proximal sleeves for attachment to said cannula, comprising:
   a parent cannula member;
   radiopaque tip means substantially softer than said parent cannula member, said tip means being constructed apart from said parent cannula member and integrally attached to the distal end of said parent cannula member by radio frequency dielectric heating so that the respective mating ends of said parent cannula member and said radiopaque tip form substantially continuous smooth external and internal wall surfaces on said composite cannula to prevent the accumulation of mucus and other bodily secretions within said cannula and to prevent injury to said patient when said composite cannula is inserted into a body cavity, duct, vessel, and the like, of said patient;

said respective mating ends of said parent cannula member and said radiopaque top abutting one another to form a joint without overlap, the outer diameter of said parent cannula member being substantially the same as the outer diameter of said tip at said joint, the outer diameter of said tip at a location distal of said joint being less than the outer diameter of said parent cannula member to form a reduced diameter portion on said tip, said reduced diameter portion distally terminating in a shoulder, said inflatable cuff being mounted on said cannula by means of said distal sleeve which engages said reduced diameter portion, the distal edge of said distal sleeve abutting said shoulder on said reduced diameter portion, thereby maintaining the continuous smooth external wall surface of said composite cannula; and a drainage opening formed in said radiopaque tip, said opening having a diameter substantially the same as the inner diameter of said parent cannula member to maintain the substantially continuous smooth internal wall surfaces of said composite cannula.

2. The composite cannula of claim 1 wherein said radiopaque means has a configuration which is distinguishable in a radiological image from bodily parts for determining the location of said cannula within said body cavity, duct, vessel, and the like, thus preventing injury to said patient by insuring proper placement of said composite cannula within said patient.

3. A unitary, integral cannula for insertion into a body cavity, duct, vessel, and the like, of a patient, said cannula being positioned within said patient by means of a radiological image, said cannula comprising:

a cannula member having a distal end;

radiopaque means separately constructed and integrally attached by a butt joint to said cannula member near said distal end of said cannula member for determining the location in said radiological image of said cannula within said body cavity, duct, vessel, and the like, said radiopaque means being substantially softer than said cannula member, thus preventing injury to said patient and insuring the proper placement of said cannula within said patient; and a reduced diameter portion and a shoulder formed on said radiopaque means distal of said joint for the attachment of an inflatable cuff, the outer diameter of said reduced diameter portion being less than the outer diameter of said radiopaque means and said cannula member at said joint, and the maximum outer diameter of said shoulder being substantially the same as that of said cannula member at said joint, said cannula having substantially continuous smooth external and internal wall surfaces.

4. The cannula of claim 3 wherein said radiopaque means comprises a preformed radiopaque tip dielectrically attached to said distal end of said cannula member, said radiopaque tip having a Shore A hardness of about 10–20 less than that of the Shore A hardness of said cannula member.

5. The cannula of claim 3 wherein said radiopaque means comprises a preformed radiopaque tip having a Shore A hardness of about 65–85.

6. The cannula of claim 3 wherein the inner and outer diameters of said cannula are substantially uniform to provide a cannula having smooth interior and exterior surfaces for preventing the accumulation of mucus and other bodily secretions within said cannula and to prevent injury to said patient.

7. A cannula for insertion into the body of a patient, said cannula being positioned by means of a radiological image, and being adapted for use with an inflatable cuff having distal and proximal sleeves, comprising:

a main cannula member; and radiopaque means for determining the location of said cannula within said patient's body without substantially obstructing the view of bodily parts, said radiopaque means being attached by abutting end surfaces of said cannula member to form a joint to provide a cannula having a homogenous structure, said radiopaque means having a portion of reduced diameter distal of said joint termination in an annular shoulder, said shoulder having a minimum outside diameter which is less than the outside diameter of said main cannula member at said joint and having a maximum outside diameter which is substantially the same as the outer diameter of said main cannula member at said joint, said distal sleeve of said inflatable cuff engaging said reduced diameter portion and abutting said shoulder to distally attach said cuff to said cannula, said distal sleeve being flush with the outside diameter of said radiopaque means to provide a cannula having a substantially smooth and continuous external wall surface.

8. The cannula of claim 7 wherein said cannula is homogenous both structurally and dimensionally.

9. The cannula of claim 7 wherein the tensile strength of said cannula is substantially uniform along its longitudinal dimension.

* * * * *